United States Patent [19]

Hope

[11] Patent Number: Plant 5,667

[45] Date of Patent: Feb. 18, 1986

[54] KALANCHOE PLANT NAMED DURANGO

[75] Inventor: Claude Hope, Cartago, Costa Rica

[73] Assignee: Pan American Plant Company, Parrish, Fla.

[21] Appl. No.: 594,487

[22] Filed: Mar. 27, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Durango characterized by its floriferous habit, producing a great abundance of brilliant orange flowers, compact growth habit, free branching, relatively early response, upright foliage, and by its adaptability to production in 10–15 cm. pots.

1 Drawing Figure

The present invention relates to a new and distinctive cultivar of Kalanchoe plant, botanically known as Kalanchoe, named Durango.

The new cultivar was referred to during the selection process by the designation (Red Glow-1-4-1-4 × Swiss Glistening Orange-2-1-4-1)-2-1, and is a product of a planned breeding program. Durango was later recoded KLV80-78N when received by Pan American Plant Co., West Chicago, Ill. in 1980. The basic objective of the breeding program was to create a new Kalanchoe cultivar having bright orange flower color, superior floriferousness, compact habit, and the ability to produce commercially acceptable quality in a year round Kalanchoe program.

The new cultivar was originated from a self-pollination of the cultivar (Red Glow-1-4-1-4 × Swiss Glistening Orange-2-1-4-1)-2 made in a controlled breeding program at Linda Vista S.A., Cartago, Costa Rica.

Durango was discovered and selected by me or a technician working under my direction, as a flowering plant within the progeny of the stated self in a field of seedlings in Cartago, Costa Rica. Asexual reproduction of the new cultivar by stem cuttings, as performed by me at Pan American Plant Co. in West Chicago, Ill. and Parrish, Fla., has demonstrated that the combination of characteristics as herein disclosed for the new cultivar are firmly fixed and are retained through successive generations of asexual reproduction.

Durango has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of Durango, which in combination distinguish this Kalanchoe as a new and distinct cultivar:

(1) Large quantity of brilliant orange flowers.

(2) Compact habit and average growth rate as compared to other cultivars.

(3) Freely branching, with shoots formed at every node.

(4) Suitable for production in 10–15 cm. pots, and flowering in 12 weeks under favorable conditions to 14 weeks under less favorable growing conditions.

(5) To reduce peduncle elongation after flower initiation, plants can be treated with B-9.

(6) Highly floriferous, with numerous flowers formed at every shoot.

(7) Foliage is very upright, leaf apex is higher than leaf base, making the plant ship easily.

The new cultivar is most similar to the cultivar Cinnabar, disclosed in U.S. Plant Pat. No. 5,160, granted Dec. 20, 1983. Durango is principally distinguished from Cinnabar by its lighter orange flower color, much smoother leaf margin, and one week earlier flower response under high temperatures.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values are taken under 7000 ft. candles of natural light at approximately 10:30 A.M. in Parrish, Fla.

Botanical classification: Kalanchoe, cv. Durango.

Parentage: Self-Pollination of the cultivar (Red Glow 1-4-1-4 × Swiss Glistening Orange -2-1-4-1)-2.

Propagation: The new cultivar holds its distinguishing characteristics through successive propagations by leaf cuttings and by division of shoots.

A. *Type cutting.*—Tip cuttings with stems up to 2 cm. long.

B. *Time to root.*—10 days at 21° C., to 14 days at 21° C. winter.

C. *Rooting habit.*—Fibrous, many very fine roots.

Plant description:

A. *Form.*—Upright, compact growth; scheduling practices can produce small plants in 10 cm. pots or large plants in 15 cm. pots.

B. *Habit of growth.*—Average growth rate for this type of plant. Shoots are formed at every node.

C. *Foliage description.*—Leaves simple, opposite, and generally symmetrical. 1. Size: Average full grown leaf of a flowering plant in a 10 cm. pot is 10–12 cm. long and 7–8 cm. wide. Plants grown in larger pots have large; full grown leaves. 2. Shape: Ovate, apex obtuse and base truncate to acute. 3. Texture: Glabrous, coriaceous, succulent. 4. Margin: Crenate, irregular. 5. Color:

Young foliage top side, 137B, under side, 132D. Mature foliage top side 147A, under side 147B.

Flowering description:

A. *Flowering habit.*—Inflorescence of each shoot is formed by dichotomous branching, staring with opening of the terminal flower of the main axis and followed by terminal flowers of the side branches of the inflorescence. Opening of new buds will continue for 2 months or more. Individual flowers will last two weeks or more after opening.

B. *Natural flowering season.*—January. Flowering time under controlled daylength at 32° C. in summer is 14 weeks; in winter at 21° C., 12 weeks. Flowering time depends on temperature, light intensity and other growing conditions.

C. *Flower buds.*—Oblong developing to tubular as petals mature. Sheathed with 4 green sepals. Corolla at maturity is about 13 mm. long. 1. Size: Up to 14 mm. long. 2. Shape: Oblong. 3. Rate of opening: Normal.

D. *Flowers borne.*—Compound dichasial cyme on strong peduncles. Peduncle length depends upon growing conditions and B-9 applications. Pedicels up to 6 mm. long.

E. *Quantity of flowers.*—Very floriferous with new flowers continuing to develop.

F. *Petals.*—1. Shape: Obovate, apex cuspidate. 2. Color: Top side when opening, 33A, fading to 35A; under side 28D. 3. Number and size of petals: 4, united in corolla; petals up to 7 mm. in diameter, total flower diameter up to 19 mm.

G. *Reproductive organs.*—1. Stamens: 8 in number. (a) Anther shape: Flat, elliptical. (b) Filament color: Yellow. (c) Ovaries: 4 celled, 7 mm. long, green.

Disease resistance:

No known Kalanchoe diseases observed to date.

General observations:

Durango is particularly characterized by an abundance of bright orange flowers, compact habit, free branching, and its leaf orientation which improves shipping ability. Durango has an average 12 week flowering response and is adaptable to production in 10–15 cm. pots.

I claim:

1. A new and distinct cultivar of Kalanchoe plant named Durango, as described and illustrated, and particularly characterized by its floriferous habit, producing a great abundance of brilliant orange flowers, compact growth habit, free branching, relatively early response, upright foliage, and by its adaptability to production in 10–15 cm. pots.

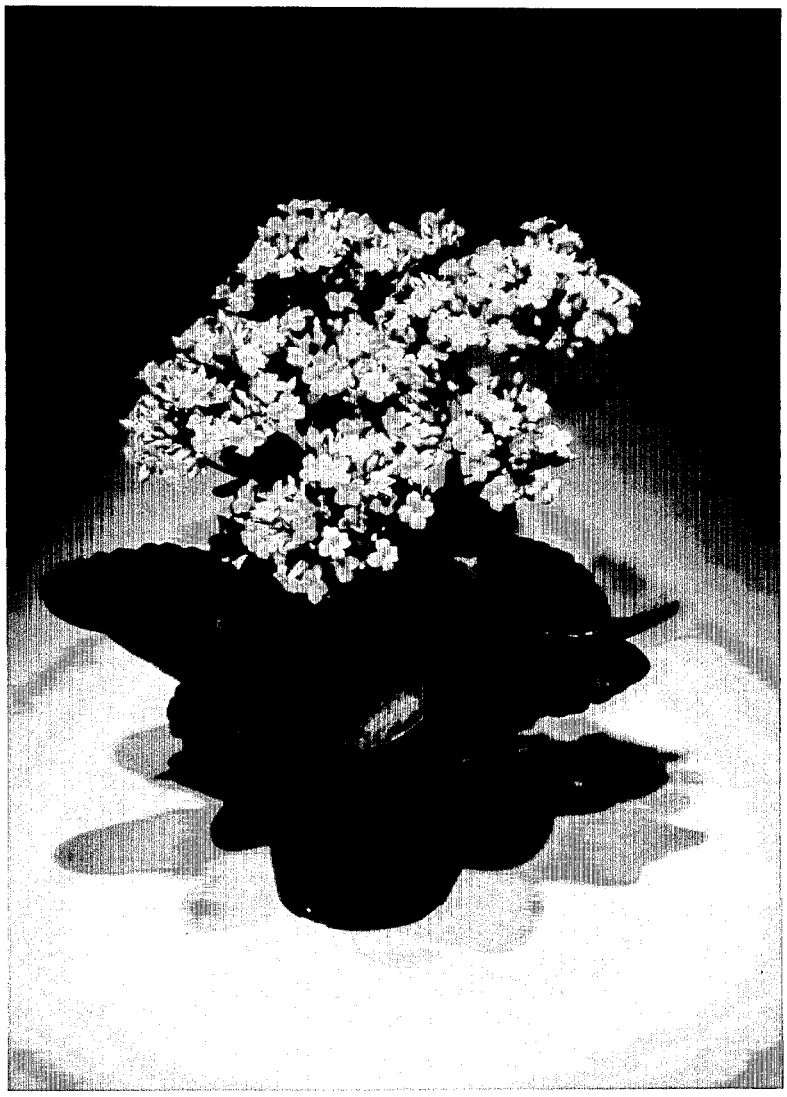

* * * * *